US00PP15686P2

(12) United States Plant Patent

Bessho et al.

(10) Patent No.: US PP15,686 P2
(45) Date of Patent: Mar. 22, 2005

(54) *CALIBRACHOA* PLANT NAMED 'KAKEGAWA S72'

(50) Latin Name: ***Calibrachoa* species**
Varietal Denomination: Kakegawa S72

(75) Inventors: Masao Bessho, Kakegawa (JP); Toshimi Ohga, Kikugawa (JP)

(73) Assignee: Sakata Seed Corporation, Yokohama (JP)

( * ) Notice: Subject to any disclaimer, the term of this patent is extended or adjusted under 35 U.S.C. 154(b) by 57 days.

(21) Appl. No.: 10/802,076
(22) Filed: Mar. 15, 2004
(51) Int. Cl.[7] ..... A01H 5/00
(52) U.S. Cl. ..... Plt./263
(58) Field of Search ..... Plt./263, 356

*Primary Examiner*—Kent Bell
(74) *Attorney, Agent, or Firm*—Jondle & Associates P.C.

(57) ABSTRACT

'Kakegawa S72' is a new variety of *Calibrachoa* plant. This new variety has dark red petal lobes with darker red petal mid-veins and dark green foliage.

1 Drawing Sheet

Genus/Species: *Calibrachoa* species.
Varietal Denomination: 'Kakegawa S72'.

BACKGROUND OF THE INVENTION

'Kakegawa S72' originated from a hybridization made in February 1999 in Kakegawa, Japan. The female parent was a *Calibrachoa* breeding line with red colored flowers and semi-creeping habit known as 9B-58C. The male parent was a *Calibrachoa* breeding line with rose colored flowers and mounding habit known as 6BC-34B-7.

In August 1999, $F_1$ seed was sown from this cross and plants were transplanted to outdoors. These plants ranged from erect to semi-creeping habit and scarlet to rose flower color. Five plants with scarlet flower color were selected and intercrossed to produce $F_2$ generation seed. In February 2000, this $F_2$ seed was sown and produced 120 plants ranging from mounding to semi-erect habit and having red to brown-red flowers. One plant with brown-red flowers and semi-creeping habit was selected for vegetative propagation. In August 2000, this selection was evaluated in the open field as plants generated from vegetative cuttings. The selection was vegetatively propagated again in February 2001 and evaluated in an open field.

The selection was further evaluated from new vegetative plants in Salinas, Calif. during 2002. The selection was subsequently named 'Kakegawa S72'. 'Kakegawa S72' was asexually reproduced by stem cuttings in Salinas, Calif. and was determined to have its characteristics firmly fixed in successive generations of asexual propagation.

DESCRIPTION FOR PHOTOGRAPH

This new *Calibrachoa* plant is illustrated by the accompanying photograph which shows blooms and foliage of the plant in full color. The colors shown being as true as can be reasonably obtained by conventional photographic procedures.

DESCRIPTION OF THE GENUS *CALIBRACHOA LLAVE & LEX*

Figure 1:
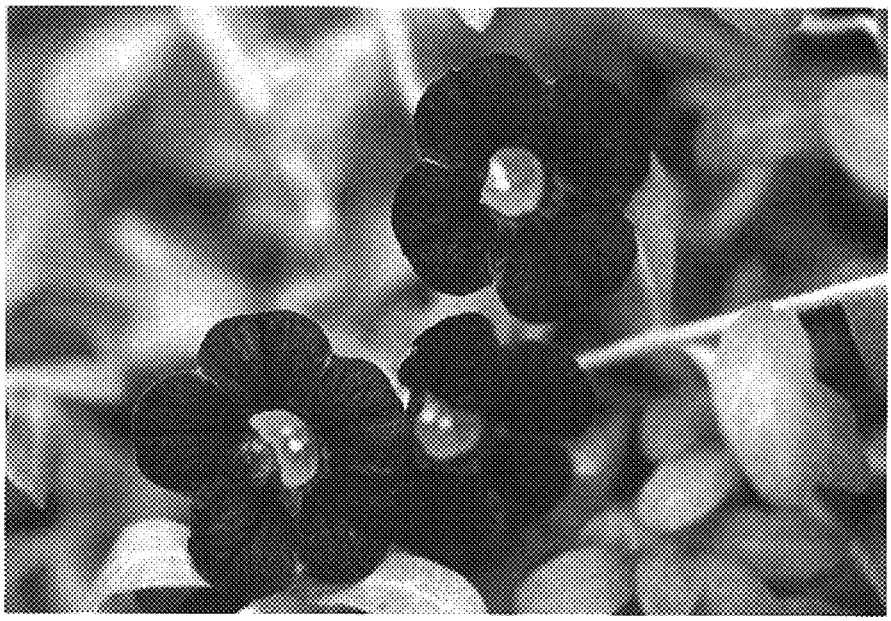
FIG. 1 shows a close-up of flowers.
Figure 2:
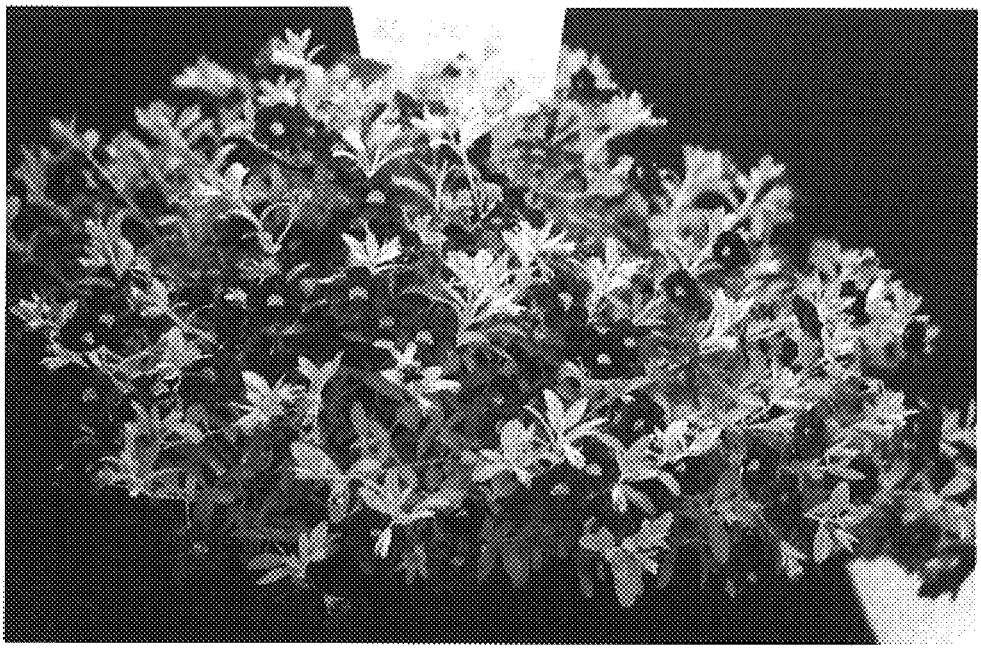
FIG. 2 shows the entire plant (known as K0-340A during testing).

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of *P. hybrida*, the Garden Petunia, and the inter-relationship of several species classified as Petunia. These studies discovered that *P. hybrida* and its ancestral species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I. N. G. Committee adopted this proposal. By 1990, Wijsman had transferred several species, including *P. parviflora* (=*C. parviflora*) to *Calibrachoa,* originally established by Llave and Lexarza in 1825. *Calibrachoa parviflora* (=*C. mexicana* Llave & Lexarza) is now the type species for the genus *Calibrachoa.*

Classification of the current Petunia and *Calibrachoa* species is still in progress. New species are also being identified. Consequently, a proper description has not been written for the *Calibrachoa* genus. *Calibrachoa* can, however, be distinguished from Petunia based on the higher chromosome number, chromosome morphology, plant branching habit and type of flower bud aestivation. Whereas Petunia species bear a flower peduncle and one new stem from a node, *Calibrachoa* bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

ENVIRONMENTAL CONDITIONS FOR PLANT GROWTH

The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 DIP 'N GROW: 9 water) root-inducing solution immediately prior to sticking into the cells trays. Cuttings were stuck into plastic cell trays having 98 cells and containing a moistened peat moss-based growing medium. The cuttings were misted with water from overhead for 10 seconds every 30 minutes until sufficient roots were formed.

Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

DETAILED DESCRIPTION OF THE NEW PLANT

Data below collected on plants three months from rooted cutting. Five plants grown in 20 cm diameter pots were transplanted to a 41 cm hanging basket. Color references are to The R.H.S. Colour Chart of The Royal Horticultural Society of London (R.H.S.). The following traits and characteristics describe the new variety.

Classification:
- *Family.*—Solanaceae.
- *Species.*—*Calibrachoa* sp.
- *Common names.*—*Calibrachoa.*

Parentage:
- *Female parent.*—Breeding line 9B-58C.
- *Male parent.*—Breeding line 6BC-34B-7.

Growth:
- *Habit.*—Decumbent.
- *Height.*—23.0 cm.
- *Spread.*—115.0 cm when grown in a 41 cm hanging basket or pot, and using five 20 cm potted plants in one hanging basket.
- *Life cycle.*—Perennial.
- *Form.*—Branching.
- *Time to produce a rooted cutting.*—6 weeks.
- *Time to bloom from propagation.*—10 weeks.
- *Flowering requirements.*—Will flower so long as day length is greater than 12 hours and temperatures exceed 13° C.
- *Resistance/susceptibility.*—Excellent resistance to rain, heat and drought. Will not tolerate temperatures below 10° C. Plants are susceptible to Botrytis, powdery mildew, various stem and root rots and certain viruses, like Tobacco Mosaic Virus and Inpatiens Necrotic Spotted Virus. Plants can be infested with aphids, leafminer, whitefly and various Lepidoptera.

Stems:
- *Stem color.*—RHS 144B (yellow-green).
- *Anthocyanin color.*—RHS N77A (purple).
- *Pubescence.*—Heavy.
- *Pubescence color.*—RHS N155A (white).
- *Stem description.*—Round.
- *Stem length.*—5.0 cm–6.0 cm.
- *Stem diameter.*—2.0 mm.
- *Internode length.*—1.5–2.5 cm.

Leaves:
- *Leaf arrangement.*—Alternate.
- *Leaf shape.*—Elliptical.
- *Leaf tip.*—Mucronate.
- *Leaf base.*—Decurrent.
- *Leaf margin.*—Entire.
- *Leaf surface.*—Rough, dull.
- *Leaf length.*—2.0 cm.
- *Leaf width.*—0.5 cm.
- *Leaf color.*—Upper surface: RHS 137A (green); lower surface: R.H.S. 139B (green).
- *Leaf surface pubescence.*—Slight.
- *Leaf surface pubescence color.*—RHS N155B (white).
- *Petiole length.*—2.0 mm.
- *Petiole color.*—RHS 138B (green).
- *Venation.*—Pinnate.

Flowers:
- *Inflorescence type.*—Solitary.
- *Flowering habit.*—Indeterminate.
- *Duration of flower life.*—6 days.
- *Shape.*—The flowers are funnel shaped with five fissures and a shallow, yet prominent, indentation of the petal tip at the mid-vein.
- *Flower depth.*—2.0 cm–2.5 cm.
- *Floral tube length.*—1.2 cm–1.5 cm.
- *Floral tube diameter.*—0.5 cm–0.7 cm.
- *Flower diameter.*—2.0 cm.
- *Calyx.*—5 sepals, free; 1.8 cm×4 mm (L×W).
- *Sepal shape.*—Lanceolate.
- *Sepal apex.*—Mucronate.
- *Sepal margin.*—Entire.
- *Sepal color.*—RHS 143A (green).
- *Bud shape.*—Ovate.
- *Bud length.*—1.5 cm.
- *Bud diameter.*—0.3 cm–0.5 cm.
- *Bud surface.*—Pubescent.
- *Bud color.*—RHS 195A (greyed-green).
- *Peduncle length.*—1.5–2.0 cm.
- *Peduncle color.*—RHS 144B (yellow-green).
- *Peduncle anthocyanin color.*—RHS N77A (purple).
- *Ovary.*—Superior.
- *Pistil number.*—1.
- *Stigma color.*—R.H.S. 150C (yellow).
- *Style color.*—R.H.S. 149B (yellow-green).
- *Corolla.*—5 petals, fused.
- *Petal shape.*—Spatulate.
- *Petal apex.*—Truncate.
- *Petal margin.*—Entire.
- *Petal pubescence.*—Glabrous.
- *Petal size.*—1.5 cm×2.0 cm.
- *Petal color.*—Lobes, upper surface: RHS 59A (red-purple) with RHS 79A (purple) petal mid-veins; lower RHS 181D (greyed-red); Corolla tube: inner RHS 7A (yellow); outer RHS 10B (yellow).
- *Stamen number.*—5, free.
- *Stamen color.*—RHS 150C (yellow-green).
- *Pollen color.*—RHS 13B (yellow).
- *Fragrance.*—Absent.
- *Seed production.*—None.

COMPARISON WITH MOST SIMILAR VARIETY

'Kakegawa S72' is a distinct variety of *Calibrachoa* owing to its dark red petal lobes with darker petal mid-veins.

'Kakegawa S72' is most similar to the variety 'Kakegawa S50' (U.S. Plant Pat. No. 14,230); however, there are differences as shown in Table 1 below.

TABLE 1

| | 'Kakegawa S72' | 'Kakegawa S50' |
|---|---|---|
| Upper Petal Color | RHS 59A (red-purple) with RHS 79A (purple) mid-veins. | Upper petal color is RHS N74B (red-purple) with RHS 77A (purple) mid-veins and corolla throat. |

TABLE 1-continued

| | 'Kakegawa S72' | 'Kakegawa S50' |
|---|---|---|
| Inner Flower Tube Color | RHS 7A (yellow) | RHS 1A (green-yellow) |

What is claimed is:

1. A new and distinct cultivar of *Calibrachoa* plant as shown and described herein.

* * * * *